United States Patent [19]
Ong

[11] Patent Number: 5,728,927
[45] Date of Patent: Mar. 17, 1998

[54] CONTROLLED MULTI-PURPOSE CHEMICAL AGENT VAPOR GENERATOR SYSTEM

[75] Inventor: Kwok Y. Ong, Aberdeen, Md.

[73] Assignee: The United States of America as represented by the Secretary of the Army, Washington, D.C.

[21] Appl. No.: 696,085

[22] Filed: Aug. 13, 1996

Related U.S. Application Data

[60] Provisional application No. 60/003,478 Sept. 8, 1995.
[51] Int. Cl.[6] ............................................. G01D 18/00
[52] U.S. Cl. ............................................. 73/1 G
[58] Field of Search ............................................. 73/1 G

[56] References Cited

U.S. PATENT DOCUMENTS

| | | |
|---|---|---|
| 4,069,701 | 1/1978 | Baldauf et al. . |
| 4,269,057 | 5/1981 | Ong et al. . |
| 5,305,630 | 4/1994 | Molozay et al. ............... 73/1 G |

Primary Examiner—Robert Raevis
Attorney, Agent, or Firm—Ulysses John Biffoni

[57] ABSTRACT

A system for generating a chemical agent airstream for testing chemical agent detection devices. The system includes subsystems for generating the chemical agent airstream, a parallel subsystem for generating an airstream for preconditioning the detection device and a subsystem for generating an interferant airstream for further determining the reliability of the detection device.

16 Claims, 2 Drawing Sheets

1

CONTROLLED MULTI-PURPOSE CHEMICAL AGENT VAPOR GENERATOR SYSTEM

GOVERNMENT INTEREST

The invention described herein may be manufactured, used or licensed by or for the U.S. government.

This application claims the benefit of provisional application 60/003,478 filed Sep. 8, 1995.

FIELD OF THE INVENTION

The invention relates to a system for generating controlled concentrations of chemical agents for testing the sensitivity of chemical agent detection devices.

BACKGROUND OF THE INVENTION

The present invention pertains generally to the field of chemical agent vapor generator systems which are used for calibrating and testing the agent sensitivity of point source chemical agent detection devices. These detection devices are typically used to detect chemical agents such as HD or mustard gas, $S(CH_2CH_2Cl)_2$, and nerve agents such as GB, $(CH_3P(O)(OR)F$ wherein $R=iC_3H_7$, and VX, $(CH_3P(O)(OC_2H_5)SR_2$ wherein $R_2$ is $CH_2CH_2N(iC_3H_7)_2$, and other highly toxic chemical vapors and aerosols. The present invention comprises an apparatus and a method for producing these and other chemical agent vapors under controlled conditions for reliably testing chemical agent detection devices located in the field or elsewhere.

Devices are generally known for testing field chemical agent detection devices. For instance, U.S. Pat. No. 4,269,057, herein incorporated by reference, discloses a device that generates chemical agent vapors and aerosols of uniform concentration under controlled agent concentrations, under controlled variable temperature conditions, and under controlled relative humidity conditions. These vapors are in turn used to test the reliability of chemical agent detection devices.

The device of the '057 patent includes, inter alia, means for producing a chemical agent-laden air stream by passing a regulated pressurized air flow to a solution of agent within a reservoir kept at a desired temperature; means for generating an air flow of controlled relative humidity and temperature; means for mixing this air flow with the agent-laden air stream, and means for exposing an agent-detector system to the mixture to test the performance of the detector system.

A second device for calibrating and checking the GB sensitivity of a point source alarm system, and similar to the device disclosed in the '057 patent, is disclosed in U.S. Pat. No. 4,069,701, herein incorporated by reference. This device is disclosed as being portable and succeeds in providing a low, constant vapor of test agent at rapid equilibration times and with a concentration of agent directly related to air flow.

Unfortunately, each of these disclosed devices is incapable of preconditioning a point source detector or early warning alarm system to be tested; these generators of the prior art do not produce interference vapors or aerosols capable of challenging the devices to be tested, and the generators themselves are hazardous in that they could produce back splash of liquid chemical agent if proper procedures are not carefully observed. The present invention overcomes these problems.

SUMMARY OF THE INVENTION

These and other objects of the invention are realized by the construction of a device that includes a means for regulating airflow over a chemical agent, means for generating a chemical agent vapor, means for generating a conditioning air, and means for generating an interferant. The preconditioning vapor allows one to calibrate or precondition the detector to atmospheric conditions such as relative humidity prior to detection of the chemical agent vapor, and the interferant as stream allows one to challenge the performance of the detector device with the chemical agent while the detector is under the influence of the potential interferant. The realized objects of the invention and the particular construction of the invention are more particularly set forth below.

DESCRIPTION OF THE PREFERRED EMBODIMENT

The system described below is constructed for the most part using commercially available components. In a preferred embodiment of the invention, the delta tube (reservoir) and manifolds of the invention are custom made glass pieces but conventional or commercial pieces can be used. Flexible TEFLON tubes or lines of 0.25 inch outer diameter are used throughout to interconnect components as described. The TEFLON minimizes absorption as well as adsorption and provides flexibility. SWAGELOK fittings and glass ball and socket joints are used to facilitate connections. Flowmeters used in the preferred embodiment are MATHESON R7640 series with needle valves to control flow rates.

Reference will now be made in detail to the present preferred embodiments of the invention, examples of which are illustrated in the accompanying drawings.

The point-source detectors to be tested by the device of the invention are required to detect toxic vapor concentrations of less than 0.1 micrograms per liter within seconds of exposure. Such detection devices, are for instance sold by Environics of Finland as M90 detector; ETG Inc. of USA as Model ICAM-APD detector; and Graseby Corp. of Great Britain, as GID3 detector. It is necessary that the systems of the present invention generate a stable but very low concentration of chemical agent vapor in order to challenge these point-source detectors.

Figure 1:
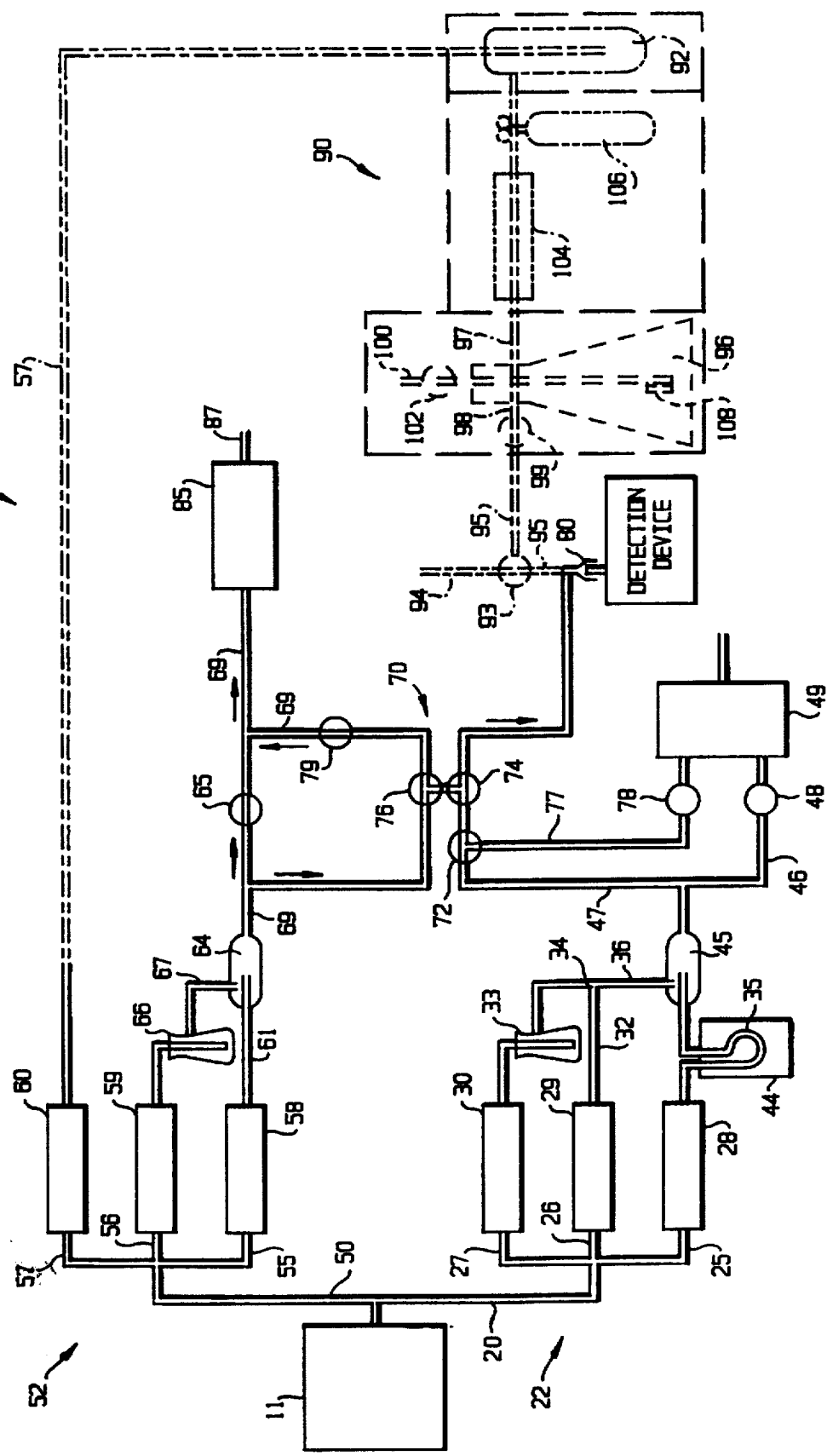
FIG. 1 is a schematic diagram of the subsystems of the device of the invention including, in phantom, means for generating interferants.

With reference to FIG. 1, the vapor generator device 10 of the invention includes an oil-less air pump compressor 11 which includes air filters (not shown). Such a device is sold under the Trademark AADCO, model number 737. This device provides a maximum flow rate of air of thirty liters/min. As shown, the compressed air generated by compressor 11 is split into two compressed air stream sources 20 and 50 for delivery to two different subsystems of the device 10—a chemical agent vapor generating subsystem 22 and a preconditioning subsystem 52.

Figure 2:
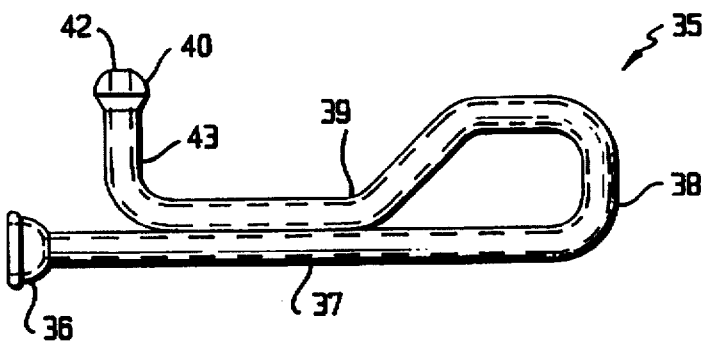
FIG. 2 is a plan view of the a vapor reservoir of the invention for storing chemical agents.

As shown, compressed air stream 20 is further split by a header into three pressurized air streams 25, 26 and 27, all moving to respective flowmeters simultaneously. Air stream 25, which is regulated by flowmeter 28, is passed to chemical vapor reservoir 35. Chemical vapor reservoir 35, in a preferred embodiment of the invention, is tubular. As shown more clearly in FIG. 2, vapor reservoir 35 is preferably of a one-piece glass construction which has a round socket joint opening 36, an elongated neck 37 extending from socket opening 36 approximately 5.13 inches in length, a U-shaped base 38 approximately 1.57 inches in length and 0.63 inches high, a curved tubular section 39 ascending from the base, and an exit port 40 defined by a ground glass ball joint 42. The outer diameter and inner diameters of the tube are generally constant and these dimensions are approximately 0.32 inches and approximately 0.19 inches respectively. As shown, the longitudinal axis 43 of exit opening 40 of reservoir 35 is perpendicular to the longitudinal axis of opening 36 and it is located in a plane approximately 1.14 inches below opening 36. Chemical vapor reservoir 35 is known as a delta tube. Delta tube 35 contains a small volume of liquid chemical agent in an amount such that the liquid only occupies the bottom portion of the tubular base 38. This volume of liquid agent fills only a portion of the base of the reservoir so as not to completely seal the tube with liquid, allowing for a continuous air flow from opening 36 to exit opening 40. A portion of the reservoir or delta tube 35, which includes at least the base 38 is preferably immersed in a temperature control bath 44 as shown in FIG. 1 or encased in a heat exchange jacket to maintain a constant desired temperature of the liquid chemical agent. Preferably the desired temperature of the chemical agent is less than the temperature of the ambient air in order to avoid liquid condensation of the effluent.

Pressurized air streams 26 and 27 are concurrently introduced in parallel streams through flow meters 29 and 30 respectively. Air stream 26 is sent to drierite column 32 and air stream 27 is sent to humidity bubbler 33. The air stream exiting drierite column 32 contains 0% relative humidity and the air stream exiting humidifier bubbler 33 contains 100% relative humidity. These two air streams are combined at T-connector 34 to create resulting air steam 36 of any desired humidity, as provided by adjusting flowmeters 29 and 30. The humidity of the resulting air stream can be estimated by calculation and/or compared to the relative humidity and temperature of preconditioning air stream 69 as measured by indicator 85 as discussed infra.

Figure 4:
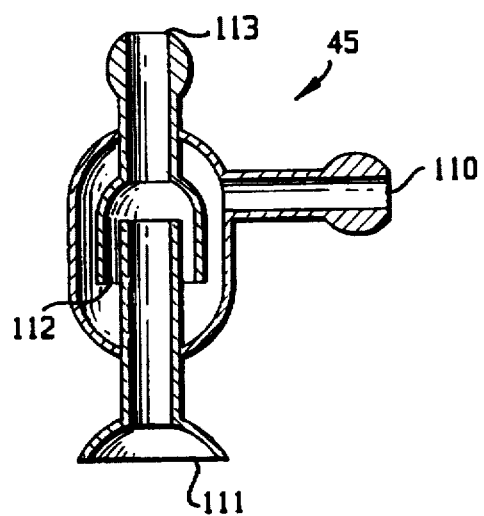
FIG. 4 shows in section and in actual size a mixing manifold of the invention.

Air stream 25 flows through delta tube 35 picking up vapors of the chemical agent and delivers the vapors to manifold 45 where the vapors are diluted by air stream 36 of desired humidity. As shown in FIG. 4, manifold 45 includes two inlets 110 and 111, a mixing chamber 112, and an exit port 113. The manifolds of the invention are designed to permit optimal results when using VX type chemical agents under high RH conditions. VX-type agents tend to decompose under high RH. The design of the manifolds minimizes such decomposition. The resulting air stream is then split into two additional air streams 46 and 47. First air stream 46 is directed to charcoal canister 49 through valve 48 where it is filtered to remove the chemical agent and then vented to the atmosphere. The second chemical agent air stream 47 is directed to solenoid subsystem 70.

By varying and controlling the flowrate through flowmeters 28, 29 and 30, the chemical agent concentration can be varied as desired. For example, a flow of 300 ml/min from flow meter 28 through delta tube 35, partially filled with mustard agent, HD, at a temperature of 100° F., combined with a dilution 36 from flowmeters 29 and 30 of 3 l/min at 10 percent relative humidity will produce an HD concentration of approximately 50 mg/m$^3$ at the sampling cup 80 at ambient temperature. As another example, a flow of 12 ml/min from flowmeter 28 through delta tube 35, partially filled with nerve agent GA, at a temperature of 0° C., combined with a dilution 36 from flowmeters 29 and 30 of 3 l/min (2.8 l/min wet, 0.2 l/min dry air) at a relative humidity of 89.5% will produce a GA concentration of approximately 0.1 mg/m$^3$ at the sampling cup 80 at ambient temperature.

Compressed air stream 50, originating from compressor 11, is directed to preconditioning subsystem 52 at the same time air stream 20 is directed to chemical agent vapor subsystem 22. Like air stream 20, air stream 50 is split into three compressed simultaneously moving air streams 55, 56 and 57. Air stream 57 may be vented, closed off by flowmeter control valve 60, or directed to interference subsystem 90 described more fully infra.

Air stream 55 is directed through drierite column 61 via flowmeter control valve 58 creating a 0% relative humidity air stream, which in turn is sent to manifold mixer 64 similar to manifold 45 shown in FIG. 4. The volumetric air flowrate from flowmeter 58 matches the combined flowrates from flowmeters 28 and 29. Air stream 56 is passed to humidifier bubbler 66 similar to bubbler 33, and a resulting water vapor laden air stream 67 is mixed with 0% relative humidity air in mixing manifold 64, creating a preconditioning airstream 69 of any desired humidity, and ideally of relative humidity substantially equal to the relative humidity of air stream 36, as provided by adjusting flowmeters 58 and 59. This airstream 69 may be vented at 87 after passing through valve 65 and after it is measured for relative humidity and temperature at indicating device 85. Airstream 69 may be used to estimate the relative humidity and temperature of resulting air stream 36 of the chemical vapor generating subsystem. Alternatively air stream 69 is directed to solenoid subsystem 70.

Figure 3A:
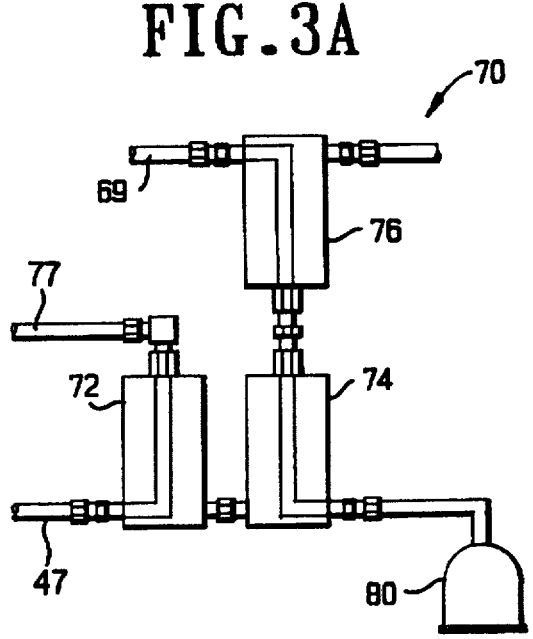
FIGS. 3A and 3B are schematic representations of the solenoid valve system of the invention.
Figure 3B:
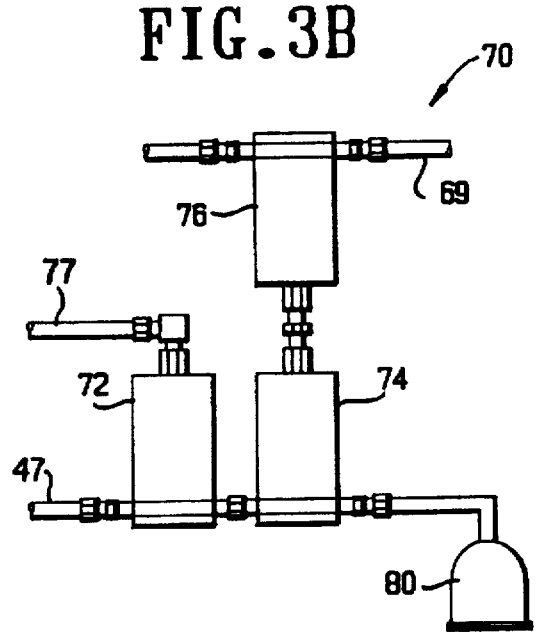

Solenoid subsystem 70 is composed of three, three-way solenoid valves 72, 74 and 76, as shown more clearly in FIGS. 3A and 3B. When the solenoids are not energized as shown in FIG. 3A, chemical agent air stream 47 enters valve 72 passes through it and is directed, via line 77 through valve 78, to filter 49 wherein it is combined with chemical agent air stream 46, filtered and exhausted to the atmosphere. In the unenergized condition, solenoid valve 74 accepts the preconditioning airstream 69 through valve 76, which in turn directs the airstream 69 to sampling cup 80 for the detection device (not shown in FIG. 3A). The subsystem 70 in the unenergized condition provides a means for preconditioning the detector prior to challenging the detector with the chemical agent, i.e., when the solenoids become energized.

When all the solenoids are in the energized condition, as shown in FIG. 3B, chemical vapor airstream 47 enters valve 72, and is passed to valve 74, which in turn directs the chemical vapor airstream to sampling cup 80. The preconditioning airstream 69, however, is directed to relative humidity and temperature detector 85 through regulation valve 79 (FIG. 1).

Shown in phantom lines is interference subsystem 90. This subsystem relies in part upon the airstream 57 originating from the preconditioning subsystem. As shown in FIG. 1 this airstream can be used to deliver any one of a number of interference airstreams to the sampling cup 80 of a detection device via line 95 and stopcock 93. In a first embodiment, airstream 57 may be directed to a container or bubbler 92 containing a volatile liquid such a gasoline or the like. As shown, the airstream is bubbled through the liquid creating an interferant airstream which is then directed to three-way stopcock 93. The three-way stopcock 93 provides a release to atmosphere via line 94 or directs the interferant airstream to sampling cup 80 via line 95 (FIG. 1) when desired. The stopcock 93 can be replaced by a three-way solenoid valve or other device having the desired flow control capability. As shown, interferant airstream vapor is directed to sampling cup 80 and is diluted with the stream coming from solenoid assembly 70 in a ratio calculated to provide the desired interference concentration. Care should be taken to determine whether the introduction of the interference stream would or would not change the final concentration of the intended chemical vapor. For example, if the additional flow significantly increased the total flow to the sampling cup, then the concentration of the intended chemical vapor must be recalculated to reflect the change. Typically, however, the "interferant airstream" is maintained in the 0.1 to 5% range which is considered to be insignificant.

In another embodiment, airstream 57 can be used as combustion air as well as a carrier for generating smoke that is delivered via stopcock 93 to sampling cup 80. To accomplish this result, a smoke-generating vessel 96 is used in place of bubbler 92. Vessel 96, for example is a heavy wall stoppered flask having an air inlet 97 for delivering combustion air to the combustion material, a smoke outlet 98 connected to line 95, a control valve 99, and a vent 100 with an associated control valve 102. The combustible material, such as saw dust, rubber particles, diesel fuel, kerosene or the like is placed in cup 108 of vessel 96. This material is ignited, for instance by a wick, and the flow rate of combustion air is adjusted to achieve good combustion. Stopcocks or control valves 99 and 100 are adjusted to ensure a proper amount of interference smoke is directed to sampling cup 80 via line 95.

In a third embodiment, air flow from airstream 57 is shut off by flowmeter control valve 60, and is replaced by a gas stream from cylinder 106 containing, for example, 0.1% ammonia in $N_2$ under pressure, which is connected to line 95 via flow control meter 104. Ammonia can then be directly delivered to sampling cup 80 where it is diluted with chemical agent airstream to, for example, a concentration of 25 ppm ammonia.

The interferant airstream can be delivered to the sampling cup concurrently with the delivery of the preconditioning airstream 69 or the chemical agent airstream 47.

The chemical vapor generator system described can be used effectively for evaluating detection devices that are designed to detect chemical vapor in concentrations of less than 0.1 micrograms per liter within seconds. The sampling cup 80 is kept as close to the solenoid assembly 70 as possible to minimize delay of delivery.

There are special considerations one must recognize in order to fully utilize the present invention. Reference is again made to FIG. 1. The regulation valves 48 and 65 are used to vent excess airflow. This may be required when generating a low concentration of chemical agent in an airstream when using highly volatile compounds, such as agent GB, to maintain a controlled airflow through solenoid subsystem 70. The airflow through the solenoid subsystem 70 is held to the minimum amount that is sufficient to meet a detector's requirements. By maintaining a minimum rate in this way, the potential for releasing excess amounts of toxic agent is minimized.

The regulation of valves 78 and 79 is required to compensate and balance out differences in internal friction as a result of differences in connecting line lengths and the restriction within the solenoid valves as well as filter canister resistance.

Flowmeters using needle valve regulation are chosen and preferred over electronic flow controllers. A needle valve, under constant pressure, will yield a characteristically smooth flow as opposed to flow controllers that will show ripples as the solenoid valve is opened and closed repeatedly for regulation. Smooth flow is critical in generating very low concentrations of toxic agents in the airstream.

Float-type flowmeters, such as the MATHESON™ R7640 Series, also provide an instant observation of flow fluctuation which is critical during system balancing. It is very difficult, if not impossible, to balance the system when digital flowmeters are used.

System balancing is achieved by turning on and off solenoid subsystem 70 repeatedly while observing all the flowmeters for disturbance. If the system is not balanced, turning the solenoids on and off will cause flow disturbances and consequently affect concentration equilibrium. To achieve system balancing, a flowmeter is connected to the sample cup 80 port of solenoid 74 to measure and adjust the flow to the sample cup using valves 48 and 65. While observing all flow meters floats and turning on and off the solenoid adjust valves 78 and 79 alternately until minimal fluctuation of floats is observed. When properly balanced, the flowmeter should remain steady when the solenoids are activated.

A mass flow indicator may be used to monitor the very low airflow for a more precise indication beyond the capability of, for instance, flowmeter 28. It is sometimes necessary to almost shut-off airflow from flowmeter 28 in order to achieve a low level chemical agent vapor generation. Under these circumstances, delta tube 35 behaves similarly to a diffusion tube, and a very low concentration from a relatively highly volatile compound is achievable.

Solenoid subsystem 70 is mounted on a flex arm positioner (not shown). This allows for moving and positioning the sampling cup on the device to be challenged.

Temperature of water bath 44 is normally kept at a temperature less than ambient temperature in order to avoid formation of condensation. Caution must be exercised not to exceed ambient temperature by only a few degrees to prevent such condensation. It may be more desirable to add additional delta tubes 35 if a single one fails to provide sufficient agent concentration.

To evaluate the detection device under other than ambient temperature, a temperature controlled chamber is required. The portion of device 10 defined from after the mixing manifolds 45 and 64 of FIG. 1 and the detection device itself are placed inside the temperature controlled chamber. Flowmeters 28, 29, 30, 58, 59 and 60 and the bubblers 33 and 66 are kept outside the temperature controlled chambers when other than ambient temperatures are being tested. It is also important to ensure zero moisture (dry conditions) within the generator system when sub-freezing temperatures are used in the chamber. In addition, percent relative humidity must be adjusted according to the temperature differential between ambient and the chamber to ensure that the desired percent relative humidity is maintained in the chamber and at the detection device.

The details of the method of construction of the generator including the size and shape of the unit do not form a critical feature of this invention and can be varied within the scope of the invention. The pressure valves, flowmeters, pump, tubes, bubblers, drierite columns and the like are conventional, commercially available units which can be varied within the skill of one in the art. It is obvious that other modifications can be made to the invention by one skilled in the art. Applicants therefore wish to be limited only by the scope of the appended claims.

What is claimed is:

1. A system for testing a chemical agent detection device, comprising:

(a) means for generating and directing a first airstream comprising a chemical agent airstream;

(b) means for generating and directing a second airstream having a controlled relative humidity;

(c) means for contacting said chemical agent airstream with said airstream having a controlled relative humidity creating a conditioned chemical agent airstream;

(d) means for generating a preconditioning airstream having a relative humidity approximately equal to that of said conditioned chemical agent airstream, so that said preconditioning airstream can be used for calibrating or preconditioning the chemical agent detection device prior to challenging the chemical agent detection device with the conditioned chemical agent airstream; and (e) means for instantaneously switching the delivery of said preconditioning airstream and said conditioned chemical agent airstream to said chemical agent detection device so that no flow disturbance occurs within the system and a steady state flow equilibrium is maintained throughout the system when flow to the detection device is switched between said preconditioning airstream and said conditioned chemical agent airstream.

2. The system of claim 1, wherein said chemical agent airstream generating means comprises a chemical agent containing reservoir, said reservoir allowing an airstream to pass over a chemical agent contained therein such that any pressure disturbance within the system will not cause a backsplash of said chemical agent from said reservoir.

3. The system of claim 2, wherein said chemical agent containing reservoir comprises a delta tube having a tubular base such that liquid chemical agent only occupies the bottom portion of said tubular base so as not to completely seal the tube with liquid agent.

4. The system of claim 2, further comprising means for maintaining the chemical agent at a controlled temperature.

5. The system of claim 2, wherein the chemical agent is selected from the group consisting of HD, GB and VX.

6. The system of claim 1, wherein said switching means comprises three three-way solenoid valves interconnected between said preconditioning airstream, said conditioned chemical agent airstream, and said chemical agent detection device.

7. The system of claim 1, further comprising means for generating an interferant airstream and means for delivering the interferant airstream to the chemical agent detection device.

8. The system of claim 7 wherein said interferant airstream comprises an airstream containing an interferant selected from the group consisting of gasoline, smoke and ammonia.

9. The system of claim 1, wherein said means for generating an airstream having a controlled relative humidity comprises:

parallel means for providing a regulated flow of pressurized air to a water bubbler and a drierite packed column respectively, said bubbler containing water through which air is passed to produce a saturated airstream of 100% relative humidity, and said drierite packs column producing an airstream of 0% relative humidity for air passed therethrough; and means for combining said airstream of 100% and 0% relative humidity so that the desired relative humidity is obtained.

10. The system of claim 1, wherein said means for generating the preconditioning airstream comprises:

a second parallel means for providing a regulated flow of pressurized air to a second water bubbler and a second drierite packed column respectively, said second bubbler containing water through which air is passed to produce a second saturated airstream of 100% relative humidity, and said second drierite packed column producing an airstream of 0% relative humidity for air passed therethrough;

means for combining said second airstream of 100% RH and said second airstream of 0% relative humidity so that said combined preconditioning airstream has the desired relative humidity; and means for measuring the relative humidity of said combined preconditioning airstream produced by said second parallel means.

11. The system of claim 1 further comprising means for generating an interferant airstream and means for delivering the interferant airstream to the chemical detection device.

12. The system of claim 1, wherein said means for contacting said chemical agent airstream with said airstream of controlled relative humidity comprises:

manifold means for adding said airstream of desired relative humidity to said chemical agent airstream.

13. A method for generating a chemical agent airstream for testing a chemical agent detection device, comprising:

(a) generating and directing a first airstream over a chemical agent generating a chemical agent airstream;

(b) generating and directing a second airstream having a controlled relative humidity;

(c) contacting said chemical agent airstream with said airstream having a controlled relative humidity creating a conditioned chemical agent airstream;

(d) generating a preconditioning airstream having a relative humidity approximately equal to said conditioned chemical agent airstream;

(e) preconditioning or calibrating the chemical agent detection device with said preconditioning airstream; and (f) instantaneously switching the flow to said detection device from said preconditioning airstream to said conditioned chemical agent airstream such that no flow disturbance occurs at said detection device and steady state flow equilibrium is maintained.

14. The method of claim 13, further comprising generating and delivering an interferant airstream to the chemical detection device.

15. The method of claim 13, further comprising challenging the chemical agent detection device with said resultant airstream containing a chemical agent following said preconditioning step.

16. The method of claim 13, wherein the chemical agent is selected for the group consisting of mustard gas (HD), GB nerve agent and VX nerve agent.

* * * * *